United States Patent [19]

Ogawa et al.

[11] Patent Number: 5,036,065
[45] Date of Patent: Jul. 30, 1991

[54] BENZOTHIADIAZEPINE DERIVATIVES

[75] Inventors: Kazuo Ogawa, Tokushima; Yoh-ichi Matsushita, Higashikurume, both of Japan

[73] Assignee: Taiho Pharmaceutical Company, Limited, Tokyo, Japan

[21] Appl. No.: 499,436

[22] PCT Filed: Oct. 18, 1989

[86] PCT No.: PCT/JP89/01069

§ 371 Date: Jun. 19, 1990

§ 102(e) Date: Jun. 19, 1990

[87] PCT Pub. No.: WO90/04590

PCT Pub. Date: May 3, 1990

[30] Foreign Application Priority Data

Oct. 20, 1988 [JP] Japan ................................ 63-264702

[51] Int. Cl.$^5$ .................... A61K 31/55; C07D 285/36
[52] U.S. Cl. ...................................... 514/211; 540/481
[58] Field of Search ......................... 540/489; 514/211

[56] References Cited

U.S. PATENT DOCUMENTS 3,453,266 7/1969 Wei et al. ............................ 540/489

Primary Examiner—Robert T. Bond
Attorney, Agent, or Firm—Armstrong, Nikaido, Marmelstein, Kubovcik & Murray

[57] ABSTRACT

The present invention provides benzothiadiazepine derivatives having the following formula and pharmaceutically acceptable salts thereof which have excellent antiarrhythmic action, local anesthetic action and calcium antagonistic action and which are very useful as cardiovascular agents such as antiarrhythmic agents and the like

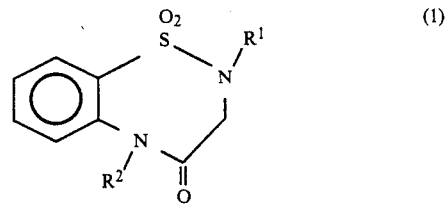

wherein $R^1$ is lower alkyl or

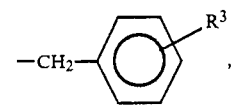

$R^3$ is hydrogen atom, lower alkoxyl or halogen atom, one or 2 to 3 same or different substituents represented by $R^3$ may be used, $R^2$ is

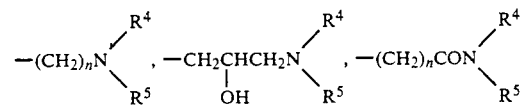

or $-(CH_2)nCO_2R^6$, n is an integer of 1 to 4, $R^4$ and $R^5$ are same or different and are each hydrogen atom or lower alkyl, $R^4$ and $R^5$ may link together to form a ring and the ring may include oxygen atom or nitrogen atom, $R^6$ is hydrogen atom or lower alkyl.

5 Claims, No Drawings

BENZOTHIADIAZEPINE DERIVATIVES

TECHNICAL FIELD

The present invention relates to novel benzothiadiazepine derivatives, pharmaceutically acceptable salts thereof and antiarrhythmic compositions comprising the derivative or salt.

BACKGROUND ART

Benzothiadiazepine derivatives are described in U.S. Pat. No. 3,453,266 and JP-B-21617/1966, whereas the pharmaceutical actions of these compounds heretofore found are limited only to antispasmodic action, hypoglycemic action, central depressant action, sedative action, hypnotic action, diuretic action, tranquillizer action and antihypertensive action. Although the compounds of the present invention have antiarrhythmic action, local anesthetic action and calcium antagonistic action, nothing has been mentioned about these actions.

An object of the present invention is to provide novel benzothiadiazepine derivatives and pharmaceutically acceptable salts thereof which have excellent antiarrhythmic action, local anesthetic action and calcium antagonistic action and which are very useful as cardiovascular agents such as antiarrhythmic agents and the like.

DISCLOSURE OF THE INVENTION

The present invention provides benzothiadiazepine derivatives represented by the formula below and pharmaceutically acceptable salts thereof

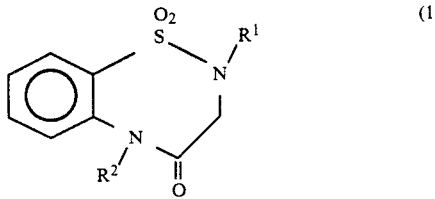

wherein $R^1$ is lower alkyl or

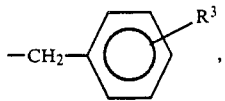

$R^3$ is hydrogen atom, lower alkoxyl or halogen atom, one or 2 to 3 same or different substituents represented by $R^3$ may be used, $R^2$ is

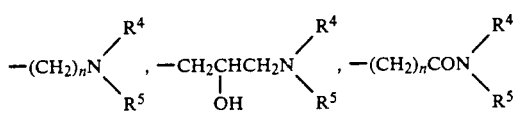

or $-(CH_2)nCO_2R^6$, n is an integer of 1 to 4, $R^4$ and $R^5$ are same of different and are each hydrogen atom or lower alkyl, $R^4$ and $R^5$ may link together to form a ring and the ring may include oxygen atom or nitrogen atom, $R^6$ is hydrogen atom or lower alkyl.

In the above formula (1), as the lower alkyl groups of $R^1$, $R^4$, $R^5$ and $R^6$ are enumerated straight-chain or branched-chain alkyl groups having 1 to 6 carbon atoms. Examples thereof are methyl, ethyl, n-propyl, isopropyl, n-butyl, isobutyl, sec-butyl, t-butyl, n-pentyl, isopentyl, n-hexyl and isohexyl. Examples of the lower alkoxyl groups as defined in $R^3$ are straight-chain or branched-chain alkoxyl groups having 1 to 3 carbon atoms, such as methoxy, ethoxy, propoxy and isopropoxy. Examples of the halogen atoms are fluorine, chlorine, bromine and iodine. Examples of the rings formed by linkage of $R^4$ and $R^5$ which contain optionally oxygen atom or nitrogen atom are pyrrolidine, piperidine, morpholine, piperazine, N-lower alkyl substituted piperazine and hydroxypiperidine.

As salts of the present compound are enumerated, for example, salts of inorganic acid such as hydrochloric acid, sulfuric acid and nitric acid, salts of aliphatic saturated monocarboxylic acid such as formic acid and acetic acid, salts of aliphatic unsaturated dicarboxylic acid such as maleic acid and fumaric acid, salts of aliphatic saturated dicarboxylic acid such as oxalic acid and malonic acid, salts of sulfonic acid such as tosilic acid and methanesulfonic acid, salts of organic acid such as picric acid, and like pharmaceutically acceptable salts. Further, in the dicarboxylic acids, also are included monoamides such as oxalic acid monoamide. As salts of the compound in which $R^2$ is $-(CH_2)nCO_2H$ are enumerated salts of alkali metal such as sodium, potassium and lithium, salts of alkaline earth metal such as calcium and magnesium and salts of basic amino acid such as lysine, alginine and histidine. Further, the present compound includes hydrates and optical isomers of the benzothiadiazepine derivatives of the formula (1).

Among the compounds of the formula (1), preferable are compounds in which, $R^1$ is methyl, benzyl, 4-methoxybenzyl, 4-chlorobenzyl, 2,4-dichlorobenzyl or 2-fluoro-4-bromobenzyl, $R^2$ is $-(CH_2)nNR^4R^5$ (n is 2 or 3, $R^4$ and $R^5$ are same or different and are each hydrogen atom, lower alkyl or link together with nitrogen atom to form pyrrolidine, piperidine, morpholine, N-methylpiperazine or 4-hydroxypiperidine ring), $-CH_2CH(OH)CH_2NR^4R^5$ ($R^4$ and $R^5$ are same or different and are each hydrogen atom, lower alkyl or link together with nitrogen atom to form pyrrolidine, piperidine, morpholine, N-methylpiperazine or 4-hydroxypiperidine ring) or $-CH_2CONR^4R^5$ ($R^4$ and $R^5$ link together with nitrogen atom to form pyrrolidine, piperidine, morpholine, N-methylpiperazine or 4-hydroxypiperidine ring). Further, most preferable are those wherein $R^1$ is methyl, benzyl, 4-methoxybenzyl or 4-chlorobenzyl, $R^2$ is dimethylaminoethyl, dimethylaminopropyl, (pyrrolidino-1-yl)ethyl, (piperidino-1-yl)propyl, (morpholino-1-yl)ethyl, (morpholino-1-yl)propyl, (4-methylpiperazino-1-yl)propyl, [2-oxo-2-(morpholino-1-yl)]ethyl, [2-oxo-2-(4-methylpiperazino-1-yl)]ethyl or [2-oxo-2-(piperidino-1-yl)]ethyl.

The present compound of the formula (1) and pharmaceutically acceptable salt thereof have excellent antiarrhythmic action, local anesthetic action and calcium antagonistic action and are very useful as cardiovascular agents such as antiarrhythmic agents and the like.

Accordingly, the present invention provides an antiarrhythmic agent comprising an effective amount of a compound of the formula (1) or pharmaceutically acceptable salt thereof, and a pharmaceutically acceptable carrier.

The present invention further provides a method of treating arrhythmia characterized by administering to a patient an effective amount of a compound of the formula (1) or pharmaceutically acceptable salt thereof.

The benzothiadiazepine derivatives (1) of the present invention can be prepared by one of the following processes (A) to (E). Compounds (2) to (6) and (8) to (10) are known.

Reaction Scheme (Process A)

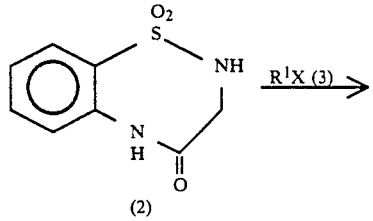

(2)

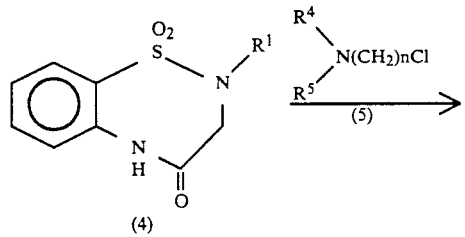

(4)

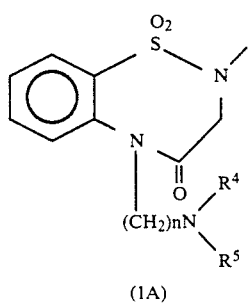

(1A)

(Process B)

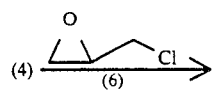

(4)

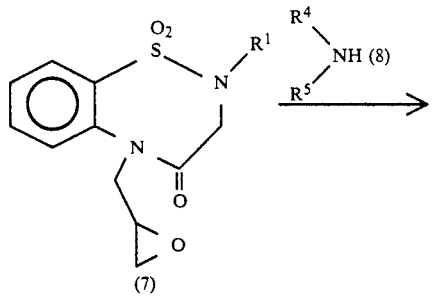

(7)

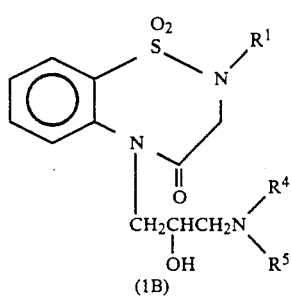

(1B)

(Process C)

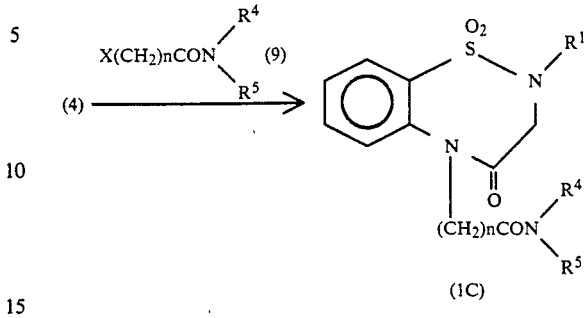

(1C)

(Process D)

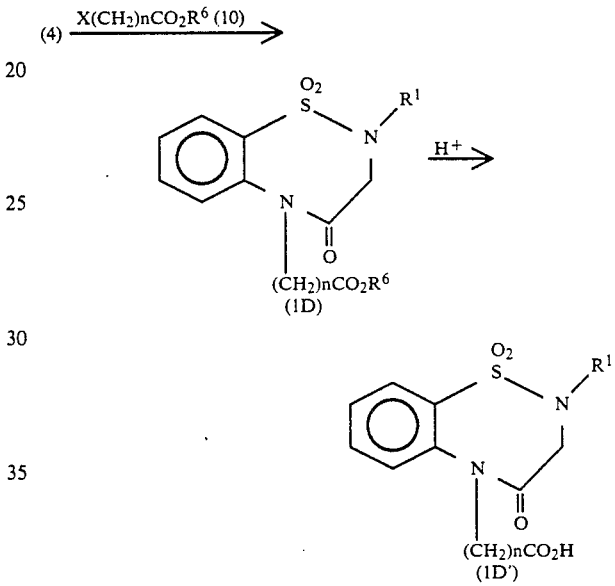

(1D')

(Process E)

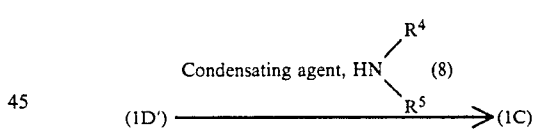

($R^1$, $R^4$, $R^5$ and $R^6$ are same as above, X is halogen atom)

Each of the processes is described below in detail.

Process A

In a solvent, the compound (2) is reacted with the compound (3) in the presence of a base as a dehalogenating agent to obtain the compound (4). The solvent is not limited specifically insofar as it does not participate in the reaction. Examples of preferred solvents are polar solvents such as N,N-dimethylformamide, N,N-dimethylacetamide and dioxane. As the base is used a metal base. Preferable examples of the base are sodium hydride, sodium amide, potassium-tert-butoxide, sodium methoxide, potassium carbonate and sodium carobonate. It is advantageous to use about 1 to 2 moles of the compound (3) and about 1.2 to 1.5 equivalents of the base per mole or equivalent of the compound (2). The reaction proceeds when conducted at room temperature to reflux temperature of the solvent, advantageously approximately at 50° to 80° C.

In a solvent, the obtained compound (4) is reacted with the compound (5) in the presence of a base to prepare the compound (1A) of the present invention. The solvent is not limited specifically insofar as it does not participate in the reaction. Examples of preferable solvents are N,N-dimethylformamide and N,N-dimethylacetamide. It is preferable to use about 1.2 to 1.5 moles of the compound (5) and about 1 to 1.2 equivalents of the base per mole or equivalent of the compound (4). The reaction proceeds when conducted at about 50° to 70° C. Examples of preferable bases are sodium hydride, n-butyl lithium and potassium-tert-butoxide.

Process B

The compound (4) obtained in the above Process A is reacted in a solvent with the compound (6) in the presence of a base to prepare the compound (7). The solvent is not limited specifically insofar as it does not participate in the reaction. Examples of preferred solvents are polar solvents such as N,N-dimethylformamide, N,N-dimethylacetamide and dioxane. It is preferable to use about 1 to 1.2 moles of the compound (6) and about 1 to 1.2 equivalents of the base per mole or equivalent of the compound (4). The reaction proceeds when conducted at room temperature to 80° C., preferably about 40 to 70° C. Examples of useful bases are sodium hydride, potassium hydride and n-butyl lithium.

The present compound (1B) is prepared by reacting the compound (7) with the compound (8) in a solvent. The solvent is not limited specifically insofar as it does not participate in the reaction. Examples of preferable solvents are methanol, ethanol and like alcohols, dichloromethane, dichloroethane and like halogenated hydrocarbons, benzene, toluene and like inert solvents. It is advantageous to use about 2 to 3 moles of the compounds (8) per mole of the compound (7). The reaction proceeds preferably at about the reflux temperature of the solvent.

Process C

The compound (4) obtained in the above Process A is reacted in a solvent with the compound (9) in the presence of a base to prepare the present compound (1C). The solvent is not limited specifically insofar as it does not participate in the reaction. Examples of preferred solvents are N,N-dimethylformamide and N,N-dimethylacetamide. It is preferable to use about 1.2 to 1.8 moles of the compound (9) and about 1 to 1.2 equivalents of the base per mole or equivalent of the compound (4). The reaction proceeds when conducted at room temperature to 80° C., preferably about 40° to 60° C. Examples of useful bases are sodium hydride, potassium hydride, n-butyl lithium and potassium carbonate.

Process D

The present compound (1D) is prepared by reacting the compound (4) obtained in the above Process A with the compound (10) in the presence of a base in a solvent. The reaction proceeds in a similar condition to the above Process C with respect to solvent, temperature, reactant proportion, base, etc. Further, the obtained compound (1D) is hydrolized in acetic acid with use of conc. HCl to obtain the present compound (1D').

Process E

As an another method of obtaining the compound (1C), the compound (1D') obtained in Process D is reacted with the compound (8) in a solvent with use of a condensating agent. The solvent is not limited specifically insofar as it does not participate in the reaction. Examples of preferred solvents are tetrahydrofuran, dioxane, dichloromethane and dichloroethane. It is preferable to use about 1.2 to 2 moles of the compound (8) per mole of the compound (1D'). The reaction proceeds when conducted at 0° C. to a reflux temperature of the solvent, preferably at 20° to 40° C. As the condensating agents are used those usually utilized for forming an acid amide. Particularly, N,N'-dicyclohexyl-carbodiimide (DCC) and diethylphosphoric acid cyanide (DEPC) are preferably used. The condensating agent is used in an amount of preferably about 1.2 to 1.5 equivalents per equivalent of the compound (1D').

The processes A to E produce the novel benzothiadiazepine derivative (1) of the present invention, which can be readily isolated by a usual separating method, such as recrystallization, column chromatography or the like.

When the benzothiadiazepine derivative of the present invention is to be administered for the purpose of effecting local anesthetic action, preventing or treating arrhythimia, or treating hypertension as calcium antagonist, the derivative is administered in the form of a pharmacological preparation such as oral preparation, injection or the like. These preparations can be produced by conventional methods already known to those skilled in the art.

Solid preparations for oral administration can be produced in a usual manner by adding to the present compound an excipient, and when required, a binder, disintegrator, lubricant, coloring agent, corrigent, flavor and the like, and making the mixture into tablets, granules, powders or an encapsulated preparation. Such additives are those generally used in the art. Examples of useful excipients are lactose, sucrose, sodium chloride, glucose, starch, calcium carbonate, kaolin, microcrystalline cellulose, silicic acid and the like. Examples of useful binders are water, ethanol, propanol, syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like. Examples of useful disintegrators are dried starch, sodium alginate, agar powder, sodium hydrogencarbonate, calcium carbonate, sodium laurylsulfate, stearic acid monoglyceride, starch, lactose and the like. Examples of useful lubricants are purified talc, stearic acid salts, borax, polyethylene glycol and the like. Examples of useful corrigents are sucrose, bitter orange peel, citric acid, tartaric acid and the like.

Liquid preparations for oral administration can be produced by adding a corrigent, buffer, stabilizer, flavor and the like to the present compound, and making the mixture into a liquid oral preparation, syrup, elixir or the like. Examples of useful corrigents are those exemplified above. Exemplary of useful buffers are sodium citrate and the like. Examples of useful stabilizers are tragacanth, gum arabic, gelatin and the like.

Injections can be produced in a usual manner by adding a pH adjusting agent, buffer, stabilizer, isotonic agent and the like to the present compound, and formulating the mixture into a preparation for subcutaneous, intramuscular or intravenous injection. Examples of useful pH adjusting agents and buffers are sodium citrate, sodium acetate, sodium phosphate and the like.

Examples of useful stabilizers are sodium pyrosulfite, EDTA, thioglycolic acid, thiolactic acid and the like.

Although the amount of the present compound to be contained in the unit form of each preparation varies with the symptoms of the patient, the type of preparation, etc., the amount is generally preferably about 1 to about 500 mg for oral administration or about 1 to about 50 mg for injection, per unit of the preparation. The dosage of the compound to be given in the form of such a preparation can not be determined specifically but varies with the symptoms, weight, age, sex, etc. of the patient. However, it is given usually at a does of about 0.1 to about 1000 mg, preferably 1 to 500 mg, per day for adults, preferably once or in up to four divided doses.

BEST MODE OF CARRYING OUT THE INVENTION

The present invention will be described below in greater detail with reference to Reference Examples and Examples.

REFERENCE EXAMPLE 1

To 5.0 g of the compound (2) in 50 ml of N,N-dimethylformamide were added 2.0 g of potassium carbonate and 6.0 g of methyl iodide and the mixture was stirred at 50° C. for 12 hours. After removing the solvent at a reduced pressure, ice and hydrochloric acid were added to the residue and the precipitates were filtered. The precipitate was recrystallized from ethanol, giving 4.0 g (yield 75%) of 2-methyl-1,2,5-benzothiadiazine-4-one (compound 4a).

melting point 214°~215° C.

REFERENCE EXAMPLE 2

The compounds 4b to 4g listed in Table 1 were prepared in the same manner as in Reference Example 1. In the elementary analysis, upper column shows calculated value, lower column analized value.

EXAMPLE 1

To 0.5 g of the compound (4a) in 30 ml of N,N-dimethylformamide was added 0.12 g of 60% sodium hydride and the mixture was stirred at room temperature for 30 minutes. Thereto was added dropwise 0.5 g of N,N-dimethylaminoethyl chloride in 10 ml of toluene and the mixture was stirred at 50° C. for 24 hours. After completion of the reaction, the solvent was distilled off and the residue was extracted twice with 30 ml of ethyl acetate. After dried over anhydrous sodium sulfate, the solvent was distilled off. The resulting residue was purified by silica gel column chromatography (eluent: chloroform/ethanol=10/1) to obtain 0.49 g of an oily product. The oil was dissolved in 30 ml of ether and thereto was added 0.19 g of maleic acid in 30 ml of ether to obtain crystals. The crystal was filtered and recrystallized from ether, giving 0.5 g (yield 55%) of the compound 1A-a.

melting point 159°~161° C.

NMR($D_2O$) δ(ppm); 2.73(3 H, s), 2.96(6 H, s), 3.37(2 H, t), 3.51(2 H, s), 4.34(2 H, t), 6.30(2 H, s), 7.60~8.05(4 H, m)

EXAMPLE 2

The compounds 1A-b to 1A-w listed in Table 2 were prepared in the same manner as in Example 1. In the elementary analysis, upper column shows calculated value, lower column analized value.

EXAMPLE 3

To 1.0 g of the compound (4a) in 20 ml of N,N-dimethylformamide was added 0.25 g of 60% sodium hydride and the mixture was stirred at room temperature for 30 minutes. Thereto were added a catalytic amount of sodium iodide and 0.5 g of epichlorohydrin (compound 6) and the mixture was stirred at room temperature for 3 days. The solvent was then distilled off, and the resulting residue was extracted by 50 ml of chloroform. The extract was dried over anhydrous sodium sulfate and the solvent was distilled off. The resulting residue was purified by silica gel column chromatography (eluent: chloroform/ethanol=20/1) to obtain 0.6 g (yield 48%) of the compound 7a.

melting point 141°~142° C.

elementary analysis (as $C_{12}H_{14}N_2O_4S$)

|  | C | H | N |
|---|---|---|---|
| Calcd. (%) | 51.05 | 5.00 | 9.92 |
| Found (%) | 50.89 | 5.02 | 9.71 |

To 0.15 g of the compound (7a) in 2 ml of dichloromethane was added 2 ml of tert-butylamine and the mixture was stirred with heating for 2 days. The solvent was distilled off and the resulting residue was purified by silica gel column chromatography (eluent: chloroform/ethanol=5/1) to obtain 0.23 g of an oily product. The oil was dissolved in 5 ml of ethanol and thereto was added 0.075 g of maleic acid in 5 ml of ethanol. The solvent was then distilled off and the residue was recrystallized from ether-isopropyl alcohol to obtain 0.12 g (yield 48%) of the compound 1 B-a.

melting point 181°~182° C.

NMR(DMSO-$d_6$) δ(ppm); 1.25(9 H, s), 2.61(3 H, s), 2.60~3.75(5 H, m), 3.90~4.30(3 H, m), 5.88(1 H, brs), 6.15(2 H, s), 7.40~8.00(4 H, m), 8.55(2 H, brs)

EXAMPLE 4

The compounds 1 B-b to 1 B-e listed in Table 3 were prepared in the same manner as in Example 3. In the elementary analysis, upper column shows calculated value, lower column analized value.

EXAMPLE 5

To 0.5 g of the compound (4c) in 20 ml of N,N-dimethylformamide was added 0.1 g of 60% sodium hydride and the mixture was stirred at room temperature for one hour. Thereto was added 0.367 mg of N-(2-chloroacetyl)piperidine and the mixture was stirred at 50° C. for 2 hours. After completion of the reaction, the solvent was distilled off and the residue was extracted with 50 ml of ethyl acetate. After washed with water and dried over anhydrous sodium sulfate, the solvent was distilled off. The resulting residue was purified by silica gel column chromatography (eluent: chloroform/methanol=9/1) to obtain 0.4 g (yield 58%) of the compound 1 C-a.

melting point 121.5°~122.5° C.

NMR($CDCl_3$) δ(ppm); 1.65(6 H, s), 3.34(2 H, s), 3.43, 3.60(each 2 H, brt), 3.77(3 H, s), 4.25(2 H, s), 4.50(2 H, s), 6.82(2 H, d), 7.20(2 H, d), 7.20~7.70(3 H, m), 7.92(1 H, d)

EXAMPLE 6

To 2.5 g of the compound (4c) in 10 ml of N,N-dimethylformamide was added 0.47 g of 60% sodium hydride and the mixture was stirred at room temperature for one hour. Thereto was added 1.92 g of tert-butyl bromoacetate and the mixture was stirred at 50° C. for 2 hours. After completion of the reaction, the solvent was distilled off and the residue was extracted with 100 ml of ethyl acetate. After washed with water and dried over anhydrous sodium sulfate, the solvent was distilled off.

The residue was recrystallized from chloroform/n-hexane to obtain 2.66 g (yield 79%) of the compound 1 D-a.

melting point 126°~127° C.

NMR(CDCl$_3$) δ(ppm); 1.50(9 H, s), 3.32(2 H, s), 3.77(3 H, s), 4.24(2 H, s), 4.31(2 H, s), 6.82(2 H, d), 7.20(2 H, d), 7.20~7.80(3 H, m), 7.94(1 H, dd)

EXAMPLE 7

The compounds 1 D-b and 1 D-c listed in Table 5 were prepared in the same manner as in Example 6. In the elementary analysis, upper column shows calculated value, lower column analized value.

EXAMPLE 8

To 2.55 g of the compound (1 D-a) were added 15 ml of acetic acid and 15 ml of 1 N-hydrochloric acid and the mixture was stirred at 90° to 100° C. for 30 minutes. After cooled, the precipitate was filtered, washed with water and dried to obtain 1.77 g (yield 79%) of the compound 1 D'.

melting point 184°~185° C.

elementary analysis (as $C_{18}H_{18}N_2O_6S$)

|  | C | H | N |
|---|---|---|---|
| Calcd. (%) | 55.38 | 4.65 | 7.18 |
| Found (%) | 55.38 | 4.71 | 7.14 |

NMR(CDCl$_3$) δ(ppm); 3.34(2 H, s), 3.72(3 H, s), 4.21(2 H, s), 4.34(2 H, s), 6.82(2 H, d), 7.21(2 H, d), 7.20~7.80(3 H, m), 7.92(1 H, d)

EXAMPLE 9

The compounds 1 D'-b and 1 D'-c listed in Table 6 were prepared in the same manner as in Example 8. In the elementary analysis, upper column shows calculated value, lower column analized value.

EXAMPLE 10

In 5 ml of dichloromethane were dissolved 0.4 g of the compound (1 D'), 0.206 g of N-methylpiperazine and 0.318 g of N,N'-dicyclohexylcarbodiimide and the solution was stirred at room temperature for one day. After completion of the reaction, the precipitate was filtered and the filtrate was concentrated. The resulting residue was purified by silica gel column chromatography (eluent: chloroform/methanol=8/1) to obtain 0.16 g (yield 33%) of the compound 1 C-c.

melting point 92°~95° C.

NMR(CDCl$_3$) δ(ppm); 2.32(3 H, s), 2.30~2.60(4 H, m), 3.33(2 H, s), 3.55, 3.74(each 2 H, t), 3.77(3 H, s), 4.25(2 H, s), 4.49(2 H, s), 6.82(2 H, d), 7.20(2 H, d), 7.20~7.70(3 H, m), 7.92(1 H, d)

EXAMPLE 11

The compounds 1 C-b, 1 C-d and 1 C-e listed in Table 4 were prepared in the same manner as in Example 10. In the elementary analysis, upper column shows calculated value, lower column analized value.

Antiarrhythmic Activity Test

The compound was tested for antiarrhythmic effect on mice with arrhythmia induced by chloroform.

Male mice of CD-1 strain weighing 22 to 27 g were used for the test, five mice in each group. The mice were intraperitoneally given 50 mg/kg of the test compound as suspended in 0.5% carboxymethylcellulose, or 0.5% carboxymethylcellulose as a control. Ten minutes after the administration, the mice were placed in a chloroform atmosphere, withdrawn therefrom after a respiratory standstill and immediately had their chest opened to observe the heart. The rhythm of ventricles of each mouse was observed with the unaided eye to check whether the rhythm was nomal or abnormal. The number of mice with normal rhythm was counted as a score.

| Compound No. | Antiarrhythmic acitivity (number of mice with normal rhythm) |
|---|---|
| 1 A-b | 5 |
| 1 A-c | 4 |
| 1 A-d | 4 |
| 1 A-k | 4 |
| 1 A-m | 5 |
| 1 A-o | 4 |
| 1 A-v | 4 |
| 1 B-d | 4 |
| 1 B-e | 4 |
| 1 C-c | 5 |
| 1 C-e | 5 |
| control | 0 |

The following are pharmaceutical preparation examples of the compound of the present invention.

Preparation Example 1

Tablet

| Compound 1 A-b | 100 mg |
|---|---|
| Lactose | 100 mg |
| Potato starch | 10 mg |
| Polyvinylpyrrolidone | 10 mg |
| Magnesium stearate | 3 mg |

By the usual method, the above ingredients in the proportions given were made into tablets each weighing about 223 mg.

Preparation Example 2

Capsule

| Compound 1 A-m | 100 mg |
|---|---|
| Lactose | 50 mg |
| Potato starch | 50 mg |
| Microcrystalline cellulose | 109 mg |
| Magnesium stearate | 1 mg |

By the usual method, the above ingredients in the proportions given were made into an encapsulated preparation in an amount of about 310 mg in each capsule.

Preparation Example 3

Injection

| Compound 1 C-c | 5 mg |
|---|---|
| Sodium chloride | 18 mg |

-continued

The above ingredients in the proportions given were made into an injection by the usual method.

TABLE 1

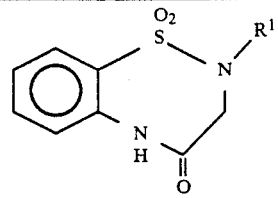

(4)

| compd. No. | R[1] | yield (%) | m.p. (°C.) | formula | elem. analysis (%) C | H | N |
|---|---|---|---|---|---|---|---|
| 4a | CH$_3$ | 75 | 214~215 | C$_9$H$_{10}$N$_2$O$_3$S | 47.78 (47.68) | 4.46 (4.48) | 12.38 (12.15) |
| 4b | —CH$_2$—⌬ | 84 | 141~142 | C$_{15}$H$_{13}$N$_2$O$_3$S | 59.59 (59.65) | 4.67 (4.65) | 9.27 (9.20) |
| 4c | —CH$_2$—⌬—OCH$_3$ | 68 | 174~176 | C$_{16}$H$_{16}$N$_2$O$_4$S | 57.82 (57.92) | 4.85 (5.06) | 8.43 (8.40) |
| 4d | —CH$_2$—⌬(Cl)(Cl) | 69 | 181~182 | C$_{15}$H$_{12}$Cl$_2$N$_2$O$_3$S | 48.53 (48.61) | 3.26 (3.37) | 7.55 (7.27) |
| 4e | —CH$_2$—⌬(F)(Br) | 88 | 186~187 | C$_{15}$H$_{12}$BrFN$_2$O$_3$S | 45.13 (45.24) | 3.02 (2.79) | 7.02 (6.96) |
| 4f | —CH$_2$CO$_2$C$_2$H$_5$ | 71 | 136~137 | C$_{12}$H$_{14}$N$_2$O$_5$S | 48.31 (48.32) | 4.73 (4.90) | 9.39 (9.33) |
| 4g | —CH$_2$—⌬—Cl | 95 | 201~202 | C$_{15}$H$_{13}$ClN$_2$O$_3$S | 53.49 (53.63) | 3.89 (3.83) | 8.32 (8.33) |

Distilled water for injections suitable amount

TABLE 2

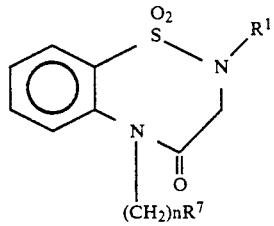

(1A)

| compd. No. | R[1] | n | R[7] | yield (%) | m.p. (°C.) | formula | elem. analysis (%) C | H | N |
|---|---|---|---|---|---|---|---|---|---|
| 1A-a | —CH$_3$ | 2 | —N(CH$_3$)$_2$ | 55 | 159~161 maleic acid salt | C$_{13}$H$_{17}$N$_3$O$_3$S (C$_4$H$_4$O$_4$) | 49.39 (49.42) | 5.61 (5.55) | 10.16 (10.12) |
| 1A-b | —CH$_2$—⌬ | 2 | —N(CH$_3$)$_2$ | 35 | 168~170 maleic acid salt | C$_{19}$H$_{23}$N$_3$O$_3$S (C$_4$H$_4$O$_4$) | 56.43 (56.37) | 5.56 (5.72) | 8.58 (8.51) |

TABLE 2-continued (1A)

[Structure: benzothiadiazine-type ring system with $SO_2$, $N-R^1$, and $N-(CH_2)_nR^7$ with C=O]

| compd. No. | $R^1$ | n | $R^7$ | yield (%) | m.p. (°C.) | formula | elem. analysis (%) C | H | N |
|---|---|---|---|---|---|---|---|---|---|
| 1A-c | $-CH_2-\bigcirc-OCH_3$ | 2 | $-N(CH_3)_2$ | 58 | 189~190 maleic acid salt | $C_{20}H_{25}N_3O_4S$ $(C_4H_4O_4)$ | 55.48 (55.38) | 5.63 (5.69) | 8.09 (8.06) |
| 1A-d | $-CH_3$ | 3 | $-N(CH_3)_2$ | 53 | 184~185 maleic acid salt | $C_{14}H_{21}N_3O_3S$ $(C_4H_4O_4)$ | 50.57 (50.71) | 5.90 (6.20) | 9.83 (9.77) |
| 1A-e | $-CH_2-\bigcirc$ | 3 | $-N(CH_3)_2$ | 20 | 123~124 picric acid salt | $C_{20}H_{25}N_3O_3S$ $(C_6H_3N_3O_7)$ | 50.65 (50.77) | 4.58 (4.67) | 13.63 (13.59) |
| 1A-f | $-CH_2-\bigcirc-OCH_3$ | 3 | $-N(CH_3)_2$ | 20 | 126~128 oxalic monoamide salt | $C_{21}H_{27}N_3O_4S$ $(C_2H_3NO_3)$ | 54.53 (54.34) | 5.97 (5.82) | 11.06 (10.94) |
| 1A-g | $-CH_3$ | 2 | $-N\bigcirc$ (pyrrolidinyl) | 43 | 162~164 maleic acid salt | $C_{15}H_{21}N_3O_3S$ $(C_4H_4O_4)$ | 51.93 (52.15) | 5.73 (5.54) | 9.56 (9.52) |
| 1A-h | $-CH_2-\bigcirc-OCH_3$ | 2 | $-N\bigcirc$ (pyrrolidinyl) | 53 | 170~172 maleic acid salt | $C_{22}H_{27}N_3O_4S$ $(C_4H_4O_4)$ | 57.24 (57.46) | 5.73 (5.64) | 7.70 (7.68) |
| 1A-i | $-CH_2-\bigcirc$ | 2 | $-N\bigcirc$ (piperidinyl) | 49 | 160~162 maleic acid salt | $C_{22}H_{27}N_3O_3S$ $(C_4H_4O_4)$ | 58.97 (58.74) | 5.90 (5.85) | 7.93 (7.75) |
| 1A-j | $-CH_2-\bigcirc-OCH_3$ | 2 | $-N\bigcirc$ (piperidinyl) | 39 | 172~173 maleic acid salt | $C_{23}H_{29}N_3O_4S$ $(C_4H_4O_4)$ | 57.95 (58.06) | 5.94 (5.69) | 7.51 (7.53) |
| 1A-k | $-CH_3$ | 3 | $-N\bigcirc$ (piperidinyl) | 39 | 203~204 HCl salt | $C_{17}H_{25}N_3O_3S$ (HCl) | 51.44 (51.47) | 6.60 (6.82) | 10.59 (10.38) |
| 1A-l | $-CH_2-\bigcirc-OCH_3$ | 3 | $-N\bigcirc$ (piperidinyl) | 51 | 165~166 HCl salt | $C_{24}H_{31}N_3O_4S$ (HCl) | 54.38 (54.70) | 6.66 (6.81) | 7.93 (7.99) |
| 1A-m | $-CH_3$ | 2 | $-N\bigcirc O$ (morpholinyl) | 40 | 143~144 | $C_{15}H_{21}N_3O_4S$ | 53.08 (53.16) | 6.23 (6.22) | 12.38 (12.29) |

TABLE 2-continued (1A)

[Structure: benzothiadiazine-type ring system with SO₂, N-R¹, and N-(CH₂)ₙR⁷ substituents, with carbonyl group]

| compd. No. | R¹ | n | R⁷ | yield (%) | m.p. (°C.) | formula | elem. analysis (%) C | H | N |
|---|---|---|---|---|---|---|---|---|---|
| 1A-n | $-CH_2-\bigcirc-OCH_3$ | 2 | $-N\bigcirc O$ (morpholine) | 24 | 179~180 maleic acid salt | $C_{22}H_{27}N_3O_5S$ $(C_4H_4O_4)$ | 55.61 (55.84) | 5.56 (5.67) | 7.48 (7.49) |
| 1A-o | $-CH_3$ | 3 | $-N\bigcirc O$ (morpholine) | 29 | 139~141 maleic acid salt | $C_{16}H_{23}N_3O_4S$ $(C_4H_4O_4)$ | 51.16 (50.98) | 5.80 (5.46) | 8.95 (8.85) |
| 1A-p | $-CH_2-\bigcirc-OCH_3$ | 3 | $-N\bigcirc O$ (morpholine) | 7 | 165~167 HCl salt | $C_{23}H_{29}N_3O_5S$ (HCl) | 55.69 (55.51) | 6.10 (6.02) | 8.47 (8.43) |
| 1A-q | $-CH_3$ | 3 | $-N\bigcirc -OH$ (4-hydroxypiperidine) | 35 | 215~217 HCl salt | $C_{17}H_{25}N_3O_4S$ (HCl) | 48.39 (48.13) | 6.45 (6.78) | 9.96 (9.72) |
| 1A-r | $-CH_2-\bigcirc-OCH_3$ | 3 | $-N\bigcirc -OH$ | 67 | oily | $C_{24}H_{31}N_3O_5S$ (HCl) | MS(M⁺)474 | | |
| 1A-s | $-CH_2-\bigcirc$ | 3 | $-N\bigcirc NCH_3$ | 40 | 185~187 maleic acid salt | $C_{23}H_{30}N_4O_3S$ $(C_8H_8O_8\cdot H_2O)$ | 53.75 (53.80) | 5.82 (5.70) | 8.09 (7.87) |
| 1A-t | $-CH_2-\bigcirc-OCH_3$ | 3 | $-N\bigcirc NCH_3$ | 47 | 180~182 maleic acid salt | $C_{24}H_{32}N_4O_4S$ $(C_8H_8O_8\cdot H_2O)$ | 53.18 (53.37) | 5.86 (5.90) | 7.75 (7.75) |
| 1A-u | $-CH_2-\bigcirc-Cl$ | 2 | $-N(CH_3)_2$ | 30 | 153~155 maleic acid salt | $C_{19}H_{22}ClN_3O_3S$ $(C_4H_4O_4)$ | 52.72 (52.96) | 5.00 (5.01) | 8.02 (7.94) |
| 1A-v | $-CH_2-\bigcirc-Cl$ | 2 | $-N\bigcirc$ (pyrrolidine) | 34 | 139~140 maleic acid salt | $C_{21}H_{24}ClN_3O_3S$ $(C_4H_4O_4)$ | 54.59 (54.90) | 5.13 (5.30) | 7.64 (7.58) |
| 1A-w | $-CH_2-\bigcirc-Cl$ | 2 | $-N\bigcirc O$ (morpholine) | 23 | 167~168 maleic acid salt | $C_{21}H_{24}ClN_3O_4S$ $(C_4H_4O_4)$ | 53.05 (52.94) | 4.99 (5.08) | 7.42 (7.38) |

TABLE 3

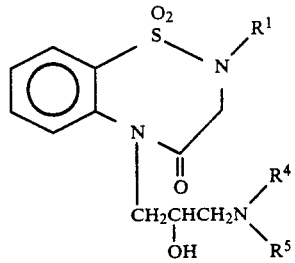
(IB)

| compd. No. | R¹ | R⁴ ... R⁵ | | yield (%) | m.p. (°C.) | formula | elem. analysis (%) C | H | N |
|---|---|---|---|---|---|---|---|---|---|
| 1B-a | —CH₃ | H | —C(CH₃)₃ | 48 | 181~182 maleic acid salt | $C_{16}H_{25}N_3O_4S$ $(C_4H_4O_4)$ | 50.95 (50.63) | 6.20 (6.15) | 8.91 (9.26) |
| 1B-b | —CH₃ | ⌐piperidine⌐ | | 75 | oily maleic acid salt | $C_{16}H_{23}N_3O_4S$ $(C_4H_4O_4)$ | MS(M⁺)353 | | |
| 1B-c | —CH₃ | ⌐N-methylpiperazine (NCH₃)⌐ | | 65 | 178~179 maleic acid salt | $C_{17}H_{26}N_4O_4S$ $(C_8H_8O_8)$ | 48.85 (48.50) | 5.58 (5.45) | 9.12 (8.92) |
| 1B-d | —CH₂—⌬—OCH₃ | ⌐piperidine⌐ | | 59 | 113~115 (HCl salt) | $C_{23}H_{29}N_3O_5S$ (HCl) | 53.74 (53.57) | 6.08 (6.19) | 8.17 (8.11) |
| 1B-e | —CH₂—⌬—OCH₃ | ⌐N-methylpiperazine (NCH₃)⌐ | | 54 | 174~175 maleic acid salt | $C_{24}H_{32}N_4O_5S$ $(C_8H_8O_8)$ | 53.33 (52.91) | 5.59 (5.40) | 7.77 (7.64) |

TABLE 4

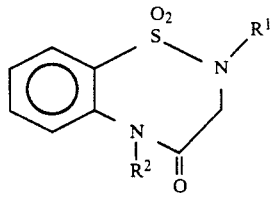
(IC)

| compd No. | R¹ | R² | yield (%) | m.p. (°C.) | formula | elem. analysis (%) C | H | N |
|---|---|---|---|---|---|---|---|---|
| 1C-a | —CH₂—⌬—OCH₃ | CH₂CON⌐piperidine⌐ | 58 | 121.5~122.5 | $C_{23}H_{27}N_3O_5S$ | 60.38 (60.50) | 5.95 (5.47) | 9.18 (9.19) |
| 1C-b | —CH₂—⌬—OCH₃ | CH₂CON⌐morpholine (O)⌐ | 62 | 133.5~135 | $C_{22}H_{25}N_3O_6S$ | 57.50 (57.21) | 5.48 (5.71) | 9.14 (8.96) |
| 1C-c | —CH₂—⌬—OCH₃ | CH₂CON⌐N-methylpiperazine (NCH₃)⌐ | 33 | 92~95 | $C_{23}H_{28}N_4O_5S$ | 58.46 (58.10) | 5.97 (5.85) | 11.86 (11.71) |
| 1C-d | —CH₃ | CH₂CON⌐piperidine⌐ | 83 | oily | $C_{16}H_{21}N_3O_4S$ | 54.64 (54.50) | 6.02 (6.23) | 11.96 (10.87) |

TABLE 4-continued

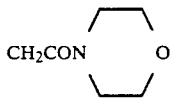

(1C)

| compd No. | R¹ | R² | yield (%) | m.p. (°C.) | formula | elem. analysis (%) C | H | N |
|---|---|---|---|---|---|---|---|---|
| 1C-e | —CH₃ | CH₂CON⟨morpholine⟩ | 65 | 182~183 | $C_{15}H_{19}N_3O_5S$ | 50.98 (51.10) | 5.42 (5.30) | 11.89 (11.83) |

TABLE 5

(1D)

Structure: benzene ring fused with S(O₂)—N(R¹)—CH₂—C(=O)—N—, with N bearing (CH₂)nCO₂R⁶

| compd. No. | R¹ | n | R⁶ | yield (%) | m.p. (°C.) | formula | elem. analysis (%) C | H | N |
|---|---|---|---|---|---|---|---|---|---|
| 1D-a | —CH₂—C₆H₄—OCH₃ | 1 | —C(CH₃)₃ | 79 | 126~127 | $C_{22}H_{26}N_2O_6S$ | 59.18 (59.50) | 5.87 (5.74) | 6.27 (6.32) |
| 1D-b | —CH₂—C₆H₃(Cl)(Cl) (2,4-dichloro) | 1 | —C₂H₅ | 81 | 135~136 | $C_{19}H_{18}Cl_2N_2O_5S$ | 49.90 (50.06) | 3.97 (3.83) | 6.13 (6.21) |
| 1D-c | —CH₂—C₆H₃(F)(Br) | 1 | —C₂H₅ | 72 | 100~102 | $C_{19}H_{18}BrFN_2O_5S$ | 47.02 (47.23) | 3.74 (3.62) | 5.77 (5.86) |

TABLE 6

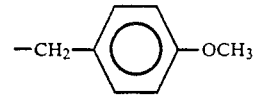

(1D′)

| compd. No. | R¹ | n | yield (%) | m.p. (°C.) | formula | elem. analysis (%) C | H | N |
|---|---|---|---|---|---|---|---|---|
| 1D′-a | —CH₂—C₆H₄—OCH₃ | 1 | 79 | 184~185 | $C_{18}H_{18}N_2O_6S$ | 55.38 (55.38) | 4.65 (4.71) | 7.18 (7.14) |

TABLE 6-continued

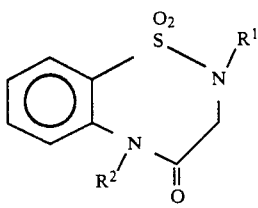

(1D')

| compd. No. | R¹ | n | yield (%) | m.p. (°C.) | formula | elem. analysis (%) C | H | N |
|---|---|---|---|---|---|---|---|---|
| 1D'-b | 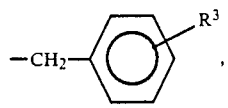 Cl —CH₂—⟨⟩—Cl | 1 | 22 | 179~180 | $C_{17}H_{14}Cl_2N_2O_5S$ | 47.57 (48.18) | 3.29 (3.36) | 6.53) (6.42) |
| 1D'-c | F —CH₂—⟨⟩—Br | 1 | 13 | 174~176 | $C_{17}H_{14}FBrN_2O_5S$ | 44.65 (43.28) | 3.09 (3.28) | 6.13 (5.91) |

We claim:

1. A benzothiadiazepine derivative represented by the formula (1) and pharmaceutically acceptable salt thereof (1)

wherein R¹ is lower alkyl or

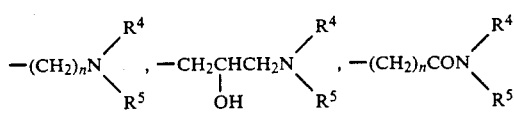

$R^3$ is hydrogen atom, lower alkoxyl or halogen atom, one or 2 to 3 same or different substituents represented by $R^3$ may be used, $R^2$ is $-(CH_2)_nN\begin{smallmatrix}R^4\\R^5\end{smallmatrix}$, $-CH_2CHCH_2N\begin{smallmatrix}R^4\\\phantom{C}\\R^5\end{smallmatrix}$, $-(CH_2)_nCON\begin{smallmatrix}R^4\\R^5\end{smallmatrix}$
$\phantom{-CH_2CHCH_2N}OH$ or $-(CH_2)nCO_2R^6$, n is an integer of 1 to 4, $R^4$ and $R^5$ are same or different and are each hydrogen atom or lower alkyl, $R^4$ and $R^5$ may link together to form a ring and the ring may include oxygen atom or nitrogen atom, $R^6$ is hydrogen atom or lower alkyl.

2. A benzothiadiazepine derivative and pharmaceutically acceptable salt thereof as defined in claim 1 wherein $R^1$ is methyl, benzyl, 4-methoxybenzyl, 4-chlorobenzyl, 2,4-dichlorobenzyl or 2-fluoro-4-bromobenzyl, $R^2$ is $-(CH_2)nNR^4R^5$ (n is 2 or 3, $R^4$ and $R^5$ are same or different and are each hydrogen atom, lower alkyl or link together with nitrogen atom to form pyrrolidine, piperidine, morpholine, N-methylpiperazine or 4-hydroxypiperidine ring), $-CH_2CH(OH)CH_2NR^4R^5$ ($R^4$ and $R^5$ are same or different and are each hydrogen atom, lower alkyl or link together with nitrogen atom to form pyrrolidine, piperidine, morpholine, N-methylpiperazine or 4-hydroxypiperidine ring) or $-CH_2CONR^4R^5$ ($R^4$ and $R^5$ link together with nitrogen atom to form pyrrolidine, piperidine, morpholine, N-methylpiperazine or 4-hydroxypiperidine ring).

3. A benzothiadiazepine derivative and pharmaceutically acceptable salt thereof as defined in claim 2 wherein $R^1$ is methyl, benzyl, 4-methoxybenzyl or 4-chlorobenzyl, $R^2$ is dimethylaminoethyl, dimethylaminopropyl, (pyrrolidino-1-yl)ethyl, (piperidino-1-yl)propyl, (morpholino-1-yl)ethyl, (morpholino-1-yl)propyl, (4-methylpiperazino-1-yl)propyl, [2-oxo-2-(morpholino-1-yl)]ethyl, [2-oxo-2-(4-methylpiperazino-1-yl)]ethyl or [2-oxo-2-(piperidino-1-yl)]ethyl.

4. An antiarrhythmic agent comprising an effective amount of a benzothiadiazepine derivative claimed in claim 1 or pharmaceutically acceptable salt thereof, and a pharmaceutically acceptable carrier or excipient.

5. A method of treating arrhythmia characterized by administering to a patient an antiarrhythmic agent calimed in claim 4.

* * * * *